(12) United States Patent
Wu et al.

(10) Patent No.: US 12,021,195 B2
(45) Date of Patent: Jun. 25, 2024

(54) ASYMMETRIC ELECTROLYTE SALTS AND BATTERIES INCORPORATING SUCH SALTS

(71) Applicant: OHIO STATE INNOVATION FOUNDATION, Columbus, OH (US)

(72) Inventors: Yiying Wu, Columbus, OH (US); William McCulloch, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 524 days.

(21) Appl. No.: 17/418,644

(22) PCT Filed: Jan. 6, 2020

(86) PCT No.: PCT/US2020/012398
§ 371 (c)(1),
(2) Date: Jun. 25, 2021

(87) PCT Pub. No.: WO2020/146274
PCT Pub. Date: Jul. 16, 2020

(65) Prior Publication Data
US 2022/0102759 A1      Mar. 31, 2022

Related U.S. Application Data

(60) Provisional application No. 62/789,854, filed on Jan. 8, 2019.

(51) Int. Cl.
*H01M 10/0568* (2010.01)
*C07C 311/09* (2006.01)
(Continued)

(52) U.S. Cl.
CPC ....... *H01M 10/0568* (2013.01); *C07C 311/09* (2013.01); *H01M 4/48* (2013.01);
(Continued)

(58) Field of Classification Search
CPC .................. C07C 311/09; H01M 10/0568
See application file for complete search history.

(56) References Cited

U.S. PATENT DOCUMENTS

| | | | |
|---|---|---|---|
| 7,923,142 B2 | 4/2011 | Matsunaga et al. | |
| 2007/0093678 A1* | 4/2007 | Umemoto | H01G 11/62 564/96 |

FOREIGN PATENT DOCUMENTS

| | | | | |
|---|---|---|---|---|
| EP | 2314572 A1 * | 4/2011 | | C07C 307/00 |
| EP | 3 050 872 B1 | 8/2016 | | |
| JP | 5181458 B2 * | 4/2013 | | C07C 303/40 |

OTHER PUBLICATIONS

International Search Report and Written Opinion on International Patent Application No. PCT/US2019/012398 dated Mar. 24, 2020 (8 pages).

(Continued)

*Primary Examiner* — Amanda C. Walke
(74) *Attorney, Agent, or Firm* — Foley & Lardner LLP

(57) ABSTRACT

The present technology is directed to fluorinated alkylsulfonamide electrolyte salts with high solubility, conductivity, and electrochemical stability as well as batteries incorporating fluorinated alkylsulfonamide salts. In any aspect and/or embodiment herein of the present technology, the battery may include a separator disposed between the cathode and the anode. The separator may be a porous paper, porous ceramic, or porous polymer separator.

20 Claims, 9 Drawing Sheets

(51) Int. Cl.
    *H01M 4/48*         (2010.01)
    *H01M 4/583*       (2010.01)
    *H01M 4/62*         (2006.01)
    *H01M 4/02*         (2006.01)

(52) U.S. Cl.
    CPC ........... *H01M 4/583* (2013.01); *H01M 4/621* (2013.01); *H01M 2004/021* (2013.01)

(56) References Cited

OTHER PUBLICATIONS

Lemaitre-Auger et al., "Poly(ethylene oxlde)-LIX rubbery electrolytes with -X-X-1, 4 disulfonamide anions having two or three ether groups in their structures", Electrochimica Acta, (2002), vol. 47, pp. 4433-4440.

Dillon et al., "Influence of the Anion on the Formation of Amorphous Ionically Conducting Lithium Salt Complexes with 18-C-6 and 2.2.2-Cryptand Macrocycles", Chem Mater, vol. 13, 2001, pp. 2516-2522.

Extended European Search Report on EP Patent Application No. 20738756.4 dated Sep. 12, 2022 (8 pages).

Lemaitre-Auger et al., "Ion-ion, short-range interactions in PEO-LiX rubbery electrolytes containing LiSCN, LiN(CF3SO2)2 or Li[CF3SO2N(CH2)3OCH3] as deduced from studies performed on PEO-LiX-KX ternary systems", Electrochimica Acta, vol. 46, 2001, pp. 1359-1367.

\* cited by examiner

ASYMMETRIC ELECTROLYTE SALTS AND BATTERIES INCORPORATING SUCH SALTS

CROSS-REFERENCE TO RELATED APPLICATIONS

This application is a U.S. National Phase Application under 35 U.S.C. § 371 of International Patent Application No. PCT/US2020/012398, filed on Jan. 6, 2020, which claims the benefit of and priority to U.S. Provisional Application No. 62/789,854, filed Jan. 8, 2019, the entire contents of each of which are incorporated herein by reference for any and all purposes.

U.S. GOVERNMENT RIGHTS

This invention was made with government support under IIP-1542995 awarded by the National Science Foundation. The government has certain rights in the invention.

FIELD

The present technology is directed to salts for electrochemical cell electrolytes as well as batteries incorporating the same.

SUMMARY

In an aspect, an electrolyte salt is provided according to Formula I

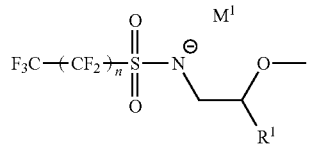

(I)

wherein
$R^1$ is H or $OCH_3$;
$M^1$ is $Li^+$, $Na^+$, $K^+$, $Rb^+$, or $Cs^+$; and
n is 0, 1, or 2;
provided that when $R^1$ is $OCH_3$ and n is 0, $M^1$ is not $Li^+$.

In an aspect, an electrolyte salt is provided according to Formula II

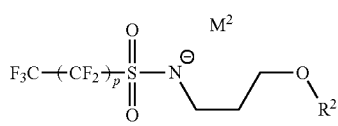

(II)

wherein
$R^2$ is $CH_3$ or $CH(CH_3)_2$;
$M^2$ is $Li^+$, $Na^+$, $K^+$, $Rb^+$, or $Cs^+$, and
p is 0, 1, or 2;
provided that when $R^2$ is $CH_3$, p is not 0.

In an aspect, an electrolyte salt is provided according to Formula III

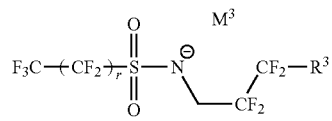

(III)

wherein
$R^3$ is F, $CF_3$, or $CF_2CF_3$;
$M^3$ is $Li^+$, $Na^+$, $K^+$, $Rb^+$, or $Cs^+$, and
r is 0, 1, or 2.

In a related aspect, a battery is provided that includes a cathode; an anode; and a non-aqueous electrolyte. The non-aqueous electrolyte includes a solvent and at least one electrolyte salt according to Formula III (provided above), Formula IV, or Formula V

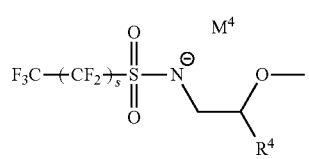

(IV)

wherein in Formula IV
$R^4$ is H or $OCH_3$;
$M^4$ is $Li^+$, $Na^+$, $K^+$, $Rb^+$, or $Cs^+$, and
s is 0, 1, or 2;

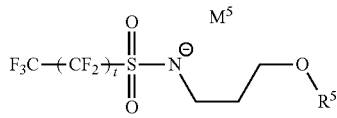

(V)

wherein in Formula V
$R^5$ is $CH_3$ or $CH(CH_3)_2$;
$M^5$ is $Li^+$, $Na^+$, $K^+$, $Rb^+$, or $Cs^+$; and
t is 0, 1, or 2.

In any embodiment herein, it may be that when $R^4$ is $OCH_3$ and s is 0, $M^4$ is not $Li^+$. In any embodiment herein, it may be that when $R^5$ is $CH_3$, t is not 0. The solvent may include dimethoxyethane, digylme, triglyme, tetraglyme, dimethylsulfoxide (DMSO), or a mixture of any two or more thereof. The battery of any embodiment disclosed herein may be a secondary battery.

DESCRIPTION OF THE DRAWINGS

(FIG. 3A) 0.2 mole fraction KMPSA, (FIG. 3B) 0.4 mole fraction KMPSA, (FIG. 3C) 0.5 mol fraction KMPSA.

DETAILED DESCRIPTION

Figure 1B:
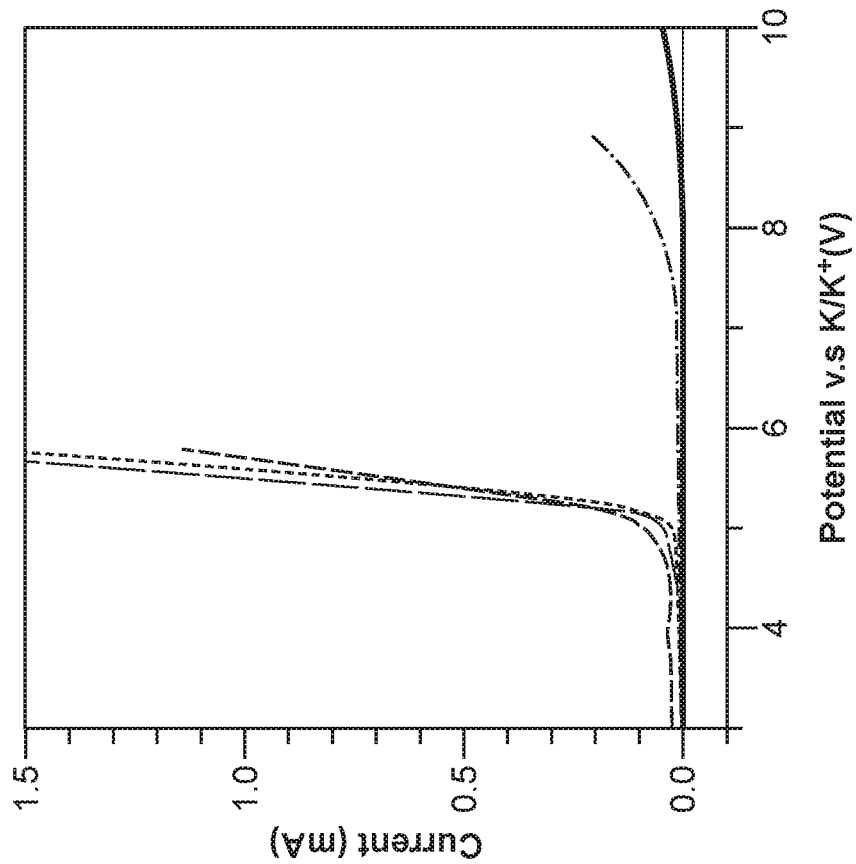
FIGS. 1A-1B provide a comparison of the solubility (FIG. 1A) and oxidative windows (FIG. 1B) between KTFSI and KMPSA in DME, according to the working examples. Salt concentrations of KTFSI increase in the order, 0.1, 0.2, and 0.33 mol fraction. KMPSA concentrations increase in the order: 0.4, 0.5, and 0.6 mol fraction. The color corresponds to the LSV of each electrolyte on a platinum working electrode.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term—for example, "about 10 wt. %" would be understood to mean "9 wt. % to 11 wt. %." It is to be understood that when "about" precedes a term, the term is to be construed as disclosing "about" the term as well as the term without modification by "about"—for example, "about 10 wt. %" discloses "9 wt. % to 11 wt. %" as well as disclosing "10 wt. %."

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

"Substantially free" as used herein will be understood by persons of ordinary skill in the art and will vary to some extent depending upon the context. If there are uses of the term which are not clear to persons of ordinary skill in the art, given the context in which it is used, "substantially free" will mean that the substance is at about 0.5 wt % or less.

The term "non-aqueous electrolyte" as used herein will be understood by persons of ordinary skill in the art and will vary to some extent depending upon the context. If there are uses of the term which are not clear to persons of ordinary skill in the art, given the context in which it is used, a "non-aqueous electrolyte" will mean an electrolyte that includes less than about 0.1 wt % $H_2O$, preferably less than about 100 ppm $H_2O$, even more preferably less than about 50 ppm $H_2O$, and further preferably less than about 20 ppm $H_2O$, prior to initial discharge of an electrochemical cell containing the electrolyte. Thus, total water content in a "non-aqueous electrolyte" may be about 1000 ppm, about 100 ppm, about 50 ppm, about 20 ppm, about 10 ppm, about 5 ppm, about 1 ppm, or any range including and/or in between any two of these values. Because complete removal of every molecule of $H_2O$ in an electrolyte is practically impossible, it is understood that an electrolyte with, e.g., less than 1000 ppm $H_2O$ prior to initial discharge includes sub-ppm levels of $H_2O$.

Throughout this disclosure, various publications, patents and published patent specifications are referenced by an identifying citation. Also within this disclosure are Arabic numerals referring to referenced citations, the full bibliographic details of which are provided immediately preceding the claims. The disclosures of these publications, patents and published patent specifications are hereby incorporated by reference into the present disclosure to more fully describe the state of the art to which this invention pertains.

The Present Technology

In an aspect, an electrolyte salt is provided according to Formula I

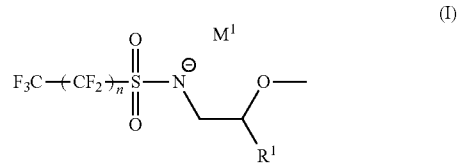

wherein
$R^1$ is H or $OCH_3$;
$M^1$ is $Li^+$, $Na^+$, $K^+$, $Rb^+$, or $Cs^+$; and
n is 0, 1, or 2;
provided that when $R^1$ is $OCH_3$ and n is 0, $M^1$ is not $Li^+$.

In an aspect, an electrolyte salt is provided according to Formula II

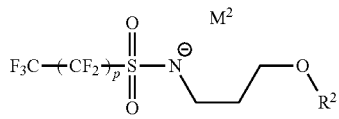
(II)

wherein
$R^2$ is $CH_3$ or $CH(CH_3)_2$;
$M^2$ is $Li^+$, $Na^+$, $K^+$, $Rb^+$, or $Cs^+$; and
p is 0, 1, or 2;
provided that when $R^2$ is $CH_3$, p is not 0.

In an aspect, an electrolyte salt is provided according to Formula III

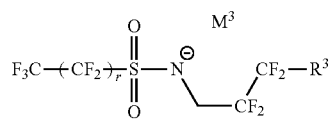
(III)

wherein
$R^3$ is F, $CF_3$, or $CF_2CF_3$;
$M^3$ is $Li^+$, $Na^+$, $K^+$, $Rb^+$, or $Cs^+$; and
r is 0, 1, or 2.

The electrolyte salt of any embodiment or aspect may be

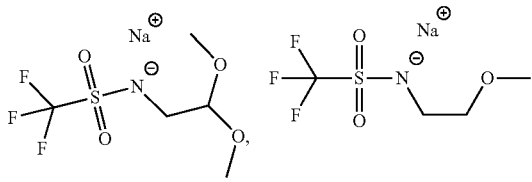

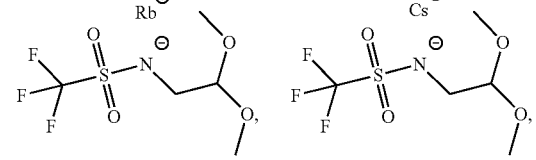

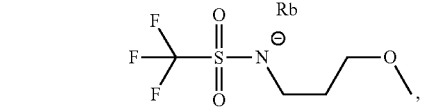

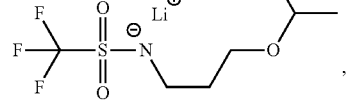

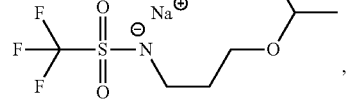

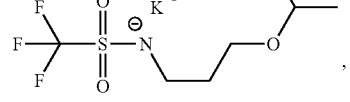

-continued

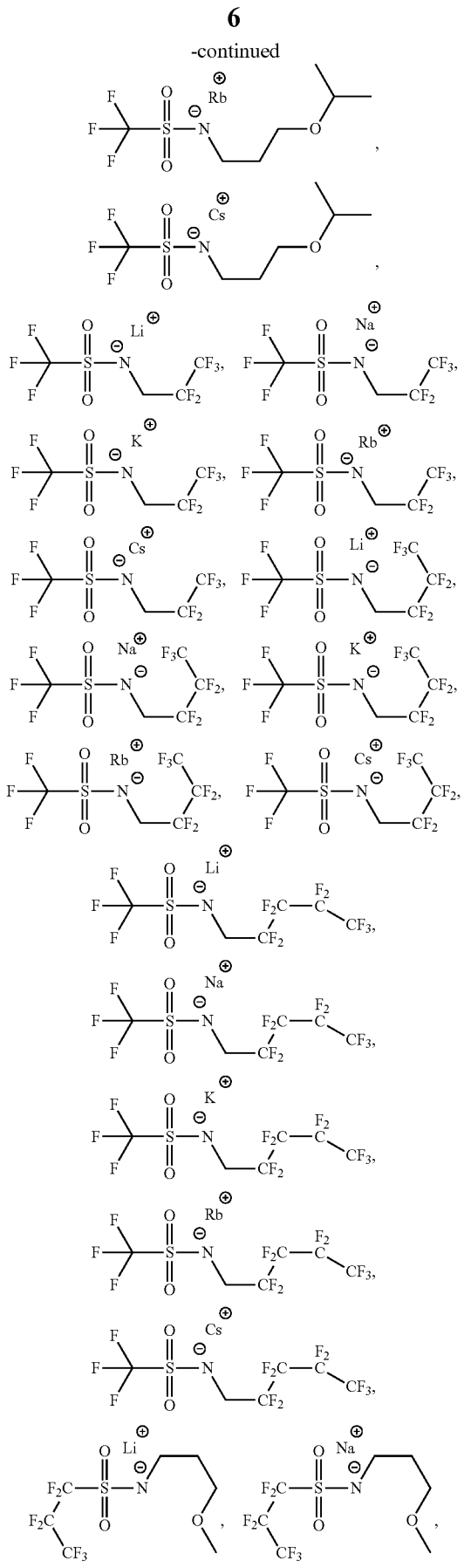

-continued

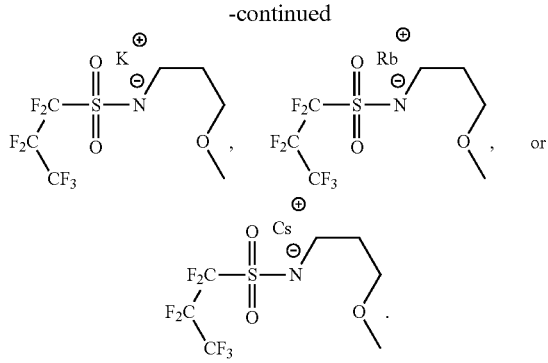

In a related aspect, a battery is provided that includes a cathode; an anode; and a non-aqueous electrolyte. The non-aqueous electrolyte includes a solvent and at least one electrolyte salt according to Formula III (provided above), Formula IV, or Formula V

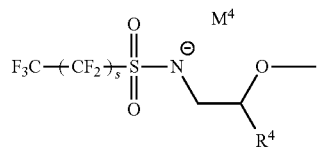
(IV)

wherein in Formula IV
$R^4$ is H or $OCH_3$;
$M^4$ is $Li^+$, $Na^+$, $K^+$, $Rb^+$, or $Cs^+$, and
s is 0, 1, or 2;

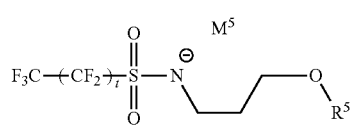
(V)

wherein in Formula V
$R^5$ is $CH_3$ or $CH(CH_3)_2$;
$M^5$ is $Li^+$, $Na^+$, $K^+$, $Rb^+$, or $Cs^+$, and
t is 0, 1, or 2.

In any embodiment herein, it may be that when $R^4$ is $OCH_3$ and s is 0, $M^4$ is not $Li^+$. In any embodiment herein, it may be that when $R^5$ is $CH_3$, t is not 0. The solvent of any embodiment herein may include dimethoxyethane, diglyme, triglyme, tetraglyme, dimethylsulfoxide (DMSO), or a mixture of any two or more thereof. In any embodiment herein, it may be that the solvent does not include a carbonate. The battery of any embodiment disclosed herein may be a secondary battery.

The concentration of the at least one electrolyte salt according to Formula III, Formula IV, or Formula V in the non-aqueous electrolyte may be about 0.05 M to about 10 M. Thus, the concentration of the at least one electrolyte salt according to Formula III, Formula IV, or Formula V in the non-aqueous electrolyte may be about 0.05 M, about 0.1 M, about 0.2 M, about 0.3 M, about 0.4 M, about 0.5 M, about 0.6 M, about 0.7 M, about 0.8 M, about 0.9 M, about 1 M, about 1.1 M, about 1.2 M, about 1.3 M, about 1.4 M, about 1.5 M, about 1.6 M, about 1.7 M, about 1.8 M, about 1.9 M, about 2 M, about 2.5 M, about 3 M, about 4 M, about 5 M, about 6 M, about 7 M, about 8 M, about 9 M, about 10 M, or any range including and/or in between any two of these values.

The at least one electrolyte salt according to Formula III, Formula IV, or Formula V of any embodiment may include one or more of

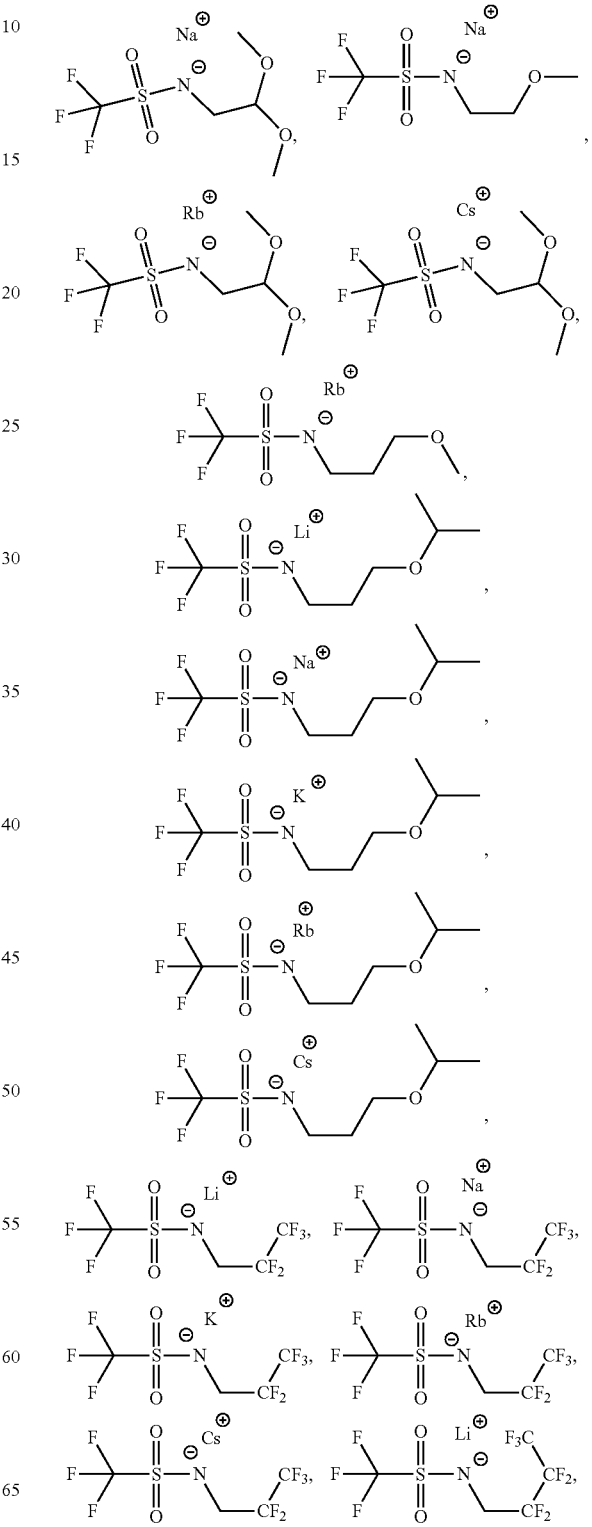

-continued

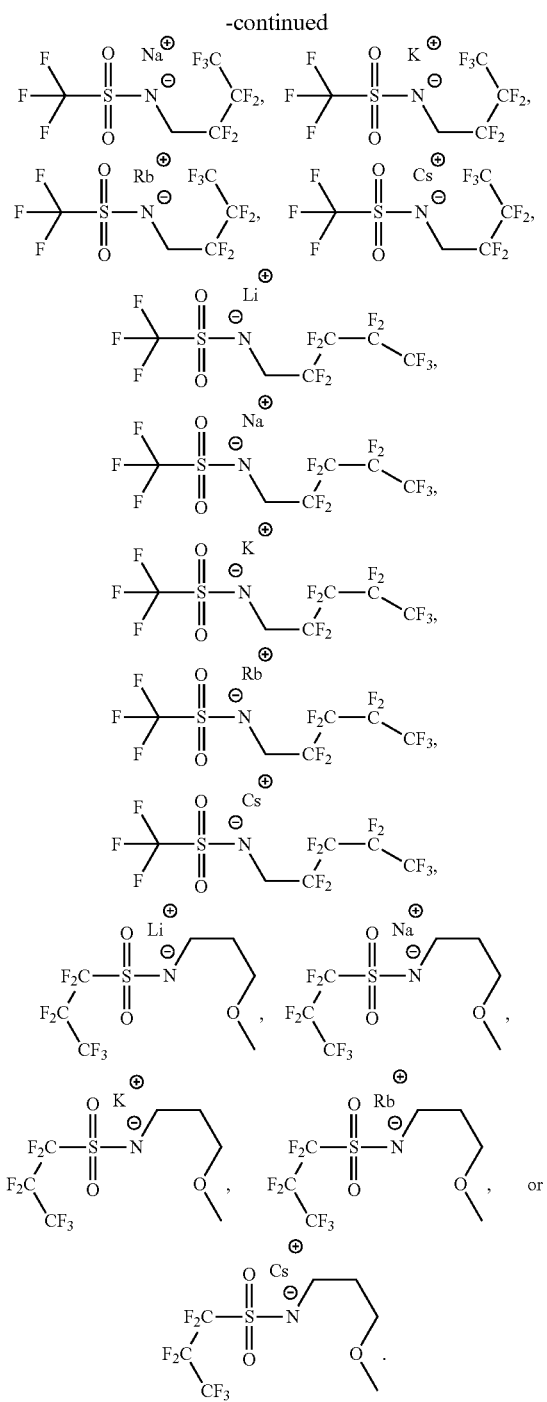

In any embodiment herein, it may be that the non-aqueous electrolyte prior to initial discharge is substantially free of salts that are not the at least one electrolyte salt according to Formula III, Formula IV, or Formula V; alternatively, in any embodiment herein, it may be the non-aqueous electrolyte further includes at least one additional salt not according to Formula III, Formula IV, or Formula V, such as $LiPF_6$, $LiBF_4$, $LiClO_4$, $LiAsF_6$, $LiCF_3SO_3$, lithium bis(oxalato)borate, lithium difluoro(oxalate)borate, $Li_2SiF_6$, $LiSbF_6$, $LiC(CF_3SO_2)_3$, lithium bis(trifluoromethanesulfonyl)imide (LiTFSI), $NaPF_6$, $NaBF_4$, $NaClO_4$, $NaAsF_6$, $NaCF_3SO_3$, sodium bis(oxalato)borate, sodium difluoro(oxalate)borate, $Na_2SiF_6$, $NaSbF_6$, $NaC(CF_3SO_2)_3$, sodium bis(trifluoromethanesulfonyl)imide (NaTFSI), $KPF_6$, $KBF_4$, $KCO_4$, $KAsF_6$, $KCF_3SO_3$, potassium bis(oxalato)borate, potassium difluoro(oxalate)borate, $K_2SiF_6$, $KSbF_6$, $KC(CF_3SO_2)_3$, potassium bis(trifluoromethanesulfonyl)imide (KTFSI), or a combination of any two or more thereof. In any embodiment herein, the at least one additional salt may be at a concentration in the non-aqueous electrolyte of about 0.05 M to about 10 M. Thus, the concentration of at least one additional salt may be about 0.05 M, about 0.1 M, about 0.2 M, about 0.3 M, about 0.4 M, about 0.5 M, about 0.6 M, about 0.7 M, about 0.8 M, about 0.9 M, about 1 M, about 1.1 M, about 1.2 M, about 1.3 M, about 1.4 M, about 1.5 M, about 1.6 M, about 1.7 M, about 1.8 M, about 1.9 M, about 2 M, about 2.5 M, about 3 M, about 4 M, about 5 M, about 6 M, about 7 M about 8 M, about 9 M, about 10 M, or any range including and/or in between any two of these values.

The anode may include an electroactive anode material. The anode of any embodiment herein may include a metal anode, such as lithium metal, sodium metal, potassium metal, or a combination of any two or more thereof; thus, the battery of any embodiment disclosed herein may be a metal-air battery, such as a lithium-air battery, a sodium-air battery, and/or a potassium-air battery. Preferably, the battery is a secondary potassium-air battery. The metal anode may or may not include a surface coating prior to initial discharge. In embodiments that are a potassium-air battery, the potassium metal of the anode may be commercial grade or of a higher purity. The potassium metal may include about 10 ppm to about 500 ppm of one or more of Al, Ba, Be, B, C, Ca, Cr, Co, Cu, Fe, Pb, Mg, Mn, Mo, Ni, Si, Ag, Na, Sr, Sn, Ti, Sb, S and V. Thus, the potassium metal may include one or more of Al, Ba, Be, B, C, Ca, Cr, Co, Cu, Fe, Pb, Mg, Mn, Mo, Ni, Si, Ag, Na, Sr, Sn, Ti, Sb, S and V where each of these may independently be included at about 10 ppm, about 20 ppm, about 30 ppm, about 40 ppm, about 50 ppm, about 60 ppm, about 70 ppm, about 80 ppm, about 90 ppm, about 100 ppm, about 110 ppm, about 120 ppm, about 130 ppm, about 140 ppm, about 150 ppm, about 160 ppm, about 170 ppm, about 180 ppm, about 190 ppm, about 200 ppm, about 220 ppm, about 240 ppm, about 260 ppm, about 280 ppm, about 300 ppm, about 350 ppm, about 400 ppm, about 450 ppm, about 500 ppm, or any range including and/or in between any two of these values. In any embodiment herein, the anode may include any one or more of the anodes described in McCulloch, W. D., et al. "Potassium-Ion Oxygen Battery Based on a High Capacity Antimony Anode," ACS Appl. Mater. Interfaces 2015, 7, 26158-26166, Ren, X., et al. "$MoS_2$ as a long-life host material for potassium ion intercalation," Nano Research 2017, 10(4), 1313-1321, and Qin, L., et al. "Localized High-Concentration Electrolytes Boost Potassium Storage in High-Loading Graphite," Adv. Energy Mater. 2019, 9, 1902618-1902624. Thus, in any embodiment herein, the anode may be intercalated with potassium—for example, one or more of Al, Ba, Be, B, C, Ca, Cr, Co, Cu, Fe, Pb, Mg, Mn, Mo, Ni, Si, Ag, Na, Sr, Sn, Ti, Sb, S, V, and graphite may be intercalated with potassium. In any embodiment herein, the anode may include Sb, $MoS_2$, or graphite intercalated with potassium. In any embodiment herein, the anode may include $K_xMoS_2$, wherein x>0.4. In any embodiment herein, the anode may include $KC_x$, wherein x is 4-50. The anode of any embodiment herein may include $K_3Sb$, $K_{0.4}MoS_2$, $KC_8$, $KC_{16}$, or $KC_{24}$. The potassium metal of any embodiment disclosed herein may include about 0 ppm to about 3000 ppm of O prior to initial discharge. Therefore, the amount of O in the potassium metal prior to initial discharge may be about 0 ppm, about 1 ppm, about 5 ppm, about 10 ppm, about 20 ppm, about 30 ppm, about 40 ppm, about 50 ppm, about 60 ppm, about 70 ppm, about 80 ppm, about 90 ppm, about 100 ppm, about 110 ppm, about 120 ppm, about 130 ppm, about 140 ppm, about 150 ppm, about 160 ppm, about 170 ppm, about 180 ppm, about 190 ppm, about 200 ppm, about 220 ppm, about 240 ppm, about 260 ppm, about 280 ppm, about 300 ppm, about 350 ppm, about 400 ppm, about 450 ppm, about 500 ppm, about 550 ppm, about 600 ppm, about 650 ppm, about 700 ppm, about 750 ppm, about 800 ppm, about 850 ppm, about 900 ppm, about 1000 ppm, about 1200 ppm, about 1400 ppm, about 1600 ppm, about 1800 ppm, about 2000 ppm, about 2200 ppm, about 2400 ppm, about 2600 ppm, about 2800 ppm, about 3000 ppm, or any range including and/or in between any two of these values. In any embodiment herein, the potassium metal of the anode may be provided by electrodeposition of potassium ions.

The anode of any aspect and/or embodiment herein may be disposed on a current collector. The current collector provides contact between the anode (e.g., potassium metal) and an external load to allow for the flow of electrons through a circuit to which the anode is connected. The current collector may be a conductive material. Illustrative current collectors include, but are not limited to, aluminum, nickel, platinum, palladium, gold, silver, copper, iron, stainless steel, rhodium, manganese, vanadium, titanium, tungsten, combinations thereof, alloys thereof, and any carbon-coated variant thereof.

The cathode of any aspect and/or embodiment herein may include positive electroactive materials. Such positive electroactive materials preferably include lithium, sodium, or potassium (also referred to herein as "potassium-containing positive electroactive materials"). By way of example, potassium-containing positive electroactive materials include, but are not limited to, olivine-based materials (such as potassium-iron-phosphates (e.g., KFePO$_4$), potassium-manganese-phosphates (e.g., KMnPO$_4$), and potassium-cobalt-phosphates (e.g., KCoPO$_4$)), fluorinated olivine-based materials (e.g., K$_2$FePO$_4$F, K$_2$MnPO$_4$F, K$_2$CoPO$_4$F), potassium-containing iron-cyano complexes (e.g., potassium Prussian blue); potassium-containing transition metal oxides (e.g., NaFeO$_2$, KCoO$_2$, KCrO$_2$, KMnO$_2$, KNiO$_2$, KNi$_{1/2}$Ti$_{1/2}$O$_2$, KNi$_{1/2}$Mn$_{1/2}$O$_2$, K$_{2/3}$Fe$_{1/3}$Mn$_{2/3}$O$_2$, KNi$_{1/3}$Co$_{1/3}$Mn$_{1/3}$O$_2$, K$_{2/3}$MnO$_2$, KMn$_2$O$_4$, K$_{2/3}$Ni$_{1/3}$Mn$_{2/3}$O$_2$), potassium-containing transition metal sulfides, and potassium-containing transition metal halides. Positive electroactive materials may be sequestered with a binder to prevent migration of the material through the cell. The binder may be any polymeric binder known for retaining the electroactive materials. Illustrative binders include, but are not limited to, one or more of poly(acrylonitrile) (PAN), polyvinylidene fluoride (PVDF), polyvinyl alcohol (PVA), polyethylene, polystyrene, polyethylene oxide, polytetrafluoroethylene (Teflon), polyacrylonitrile, polyimide, styrene butadiene rubber (SBR), carboxy methyl cellulose (CMC), gelatin, a co-polymer of any two or more such polymers, or a blend of any two or more such polymers. The cathode may include a carbon material, such as microporous carbon, mesoporous carbon, mesoporous microbeads, graphite, expandable graphite, carbon black, carbon nanotubes, or a mixture of any two or more thereof. Commercial examples of carbon black include, but are not limited to, Super P, Black Pearl 2000, Denka Black, Vulcan XC72R, and Ketjen black. The cathode may be disposed on a current collector, such as aluminum, nickel, platinum, palladium, gold, silver, copper, iron, stainless steel, rhodium, manganese, vanadium, titanium, tungsten, combinations thereof, alloys thereof, and any carbon-coated variant thereof, where the current collector may be a foil, mesh, or screen.

The cathode of any aspect and/or embodiment herein may be an air cathode, such that the battery of any aspect and/or embodiment herein is a metal-air battery (e.g., a potassium-air secondary battery). The air cathode may include a porous carbon material, such as a high surface area porous carbon material, where illustrative examples include microporous carbon, mesoporous carbon, mesoporous microbeads, graphite, expandable graphite, carbon black, or carbon nanotubes. Commercial examples of carbon black are provided above. The air cathode may optionally include a metal-based catalyst with the porous carbon material, where the optional metal-based catalyst in the air cathode is used for promoting the reaction of the air with the potassium and the decomposition of the discharged product back to its original state. The metal-based catalyst may include one or more of Ir, Pt, Pd, Fe, Ti, Zr, Zn, Ag, Au, Ni, Co, Mn, Ce or La. Suitable metal catalysts include, but are not limited to, metal oxides such as MnO$_2$, Fe$_3$O$_4$, PdO, NiO, Ni$_2$O$_3$, Co$_3$O$_4$, CuO, and TiO$_2$. However, the air cathode may be free of a metal-based catalyst.

The porous carbon material of the air cathode may be sequestered with a binder to prevent migration of the material through the cell. For example, the porous carbon material may be intimately mixed with a binder either by heating of the binder to a liquid state or in solution with a solvent. In the former case, a molten mixture of the porous active carbon material and the binder are place in a mold and cooled to solidify the binder. In the latter case, the porous active carbon material, binder, and solvent are mixed, placed into a form or mold, and the solvent removed. The binder may be any polymeric binder known for retaining the electroactive materials. Illustrative binders include, but are not limited to, one or more of poly(acrylonitrile) (PAN), polyvinylidene fluoride (PVDF), polyvinyl alcohol (PVA), polyethylene, polystyrene, polyethylene oxide, polytetrafluoroethylene (Teflon), polyacrylonitrile, polyimide, styrene butadiene rubber (SBR), carboxy methyl cellulose (CMC), gelatin, a co-polymer of any two or more such polymers, or a blend of any two or more such polymers. Loading of the carbon in the binder should be sufficient to support electron transfer in the cell and provide a sufficient cell voltage. For example, the loading may be from about 0.1 mg$_{carbon}$/cm$^2$ to about 2 mg$_{carbon}$/cm$^2$, such as from about 0.5 mg$_{carbon}$/cm$^2$ to about 1.5 mg$_{carbon}$/cm$^2$. For example, the loading may be about 1.0 mg$_{carbon}$/cm$^2$.

The air cathode may also include a gas-diffusion layer (GDL) upon which the porous carbon material is disposed. The GDL allows for additional oxygen passage into the cell for better, and more even distribution of the oxygen throughout the cell. GDL materials may include, but are not limited to, paper and polymers. The porous carbon material may be sequestered on a current collector, such as carbon paper, aluminum, nickel, platinum, palladium, gold, silver, copper, iron, stainless steel, rhodium, manganese, vanadium, titanium, tungsten, combinations thereof, alloys of any two or more of these metals, and any carbon-coated variant of such metals, combinations, and/or alloys. The current collector may be a foil, mesh, or screen.

The batteries of the present technology may take any form as is known for such batteries. For example, a battery of the present technology may be a coin cell, the structure of which is generally well known. For a metal-air battery that is a coin cell, the cathode side of the coin cell may contain a shell covering that is porous or has holes in it to allow for air penetration into the cell, while the anode side of the coin cell is a solid shell. Electrical contacts are made with the outer surface of the shell. According to other exemplary embodiments, other types of batteries may be employed using the present technology.

In any aspect and/or embodiment herein of the present technology, the battery may include a separator disposed between the cathode and the anode. The separator may be a porous paper, porous ceramic, or porous polymer separator. Illustrative separators include, but are not limited to, polyimide, polyethylene, Celgard polymer separator, paper, glass (e.g., glass fibers), and ceramics.

The examples herein are provided to illustrate advantages of the present technology and to further assist a person of ordinary skill in the art with preparing or using the present technology. The examples herein are also presented in order to more fully illustrate the preferred aspects of the present technology. The examples should in no way be construed as limiting the scope of the present technology. The examples can include or incorporate any of the variations, aspects or embodiments of the present technology described above. The variations, aspects or embodiments described above may also further each include or incorporate the variations of any or all other variations, aspects or embodiments of the present technology.

EXAMPLES

Experimental Details

Materials Trifluoromethanesulfonic anhydride (99.5%) and 2,2,3,3,3-pentafluoropropylamine (97%) were purchased from Oakwood Chemical. Triethylamine (TEA) (>99%), diglyme (99.5%), aminoacetaldehyde dimethyl acetal (99%), 3-methoxypropylamine (99%) were purchased from Sigma Aldrich. Lithium hydride (>97%) was purchased from Alfa Aesar. 1H,1H-heptafluorobutylamine (>95%) was purchased from TCI research chemicals. Aluminum foil was purchased from MTI corp. and punched into discs with an area of 1.77 $cm^2$.

Synthesis of Acid Sulfonamides. In general, 84 mmol (0.95 eq) of the desired primary amine and 126 mmol (1.5 eq, 17.7 mL) of triethylamine were dissolved in 180 mL of dry dichloromethane within a 1 L round bottom flask. Then, 88 mmol (1.0 eq, 25 g) of trifluoromethanesulfonic anhydride was dissolved in 80 mL of dry dichloromethane and added to a 125 mL addition funnel which was then attached to the 1 L round bottom flask. The funnel was sealed with a rubber septum purged with argon. The 1 L reaction flask was lowered to −78° C. and the contents stirred at 300 rpm. The trifluoromethanesulfonic anhydride/dichloromethane solution was then added drop wise at a rate of ~1.5 mL/min. After complete addition of the anhydride, the cooling bath was removed and the reaction was allowed to warm to room temperature naturally. Once the reaction reached room temperature, it was stirred for an additional 5 hours under argon to ensure complete reaction.

After complete reaction, the majority of the dichloromethane solvent was removed using a rotary evaporator. 35 mL of 4 M NaOH was added to the crude product and added to an extraction funnel. The aqueous layer was extracted with dichloromethane (3×, 40 mL) to remove any organic byproducts and triethylamine. The aqueous layer was then collected and brought to a pH<4 with 5 M HCl to fully protonate the sulfonamide. At this point, the sulfonamide became less soluble in water resulting in a cloudy solution. The resulting acidic aqueous solution was extracted with dichloromethane (3×, 40 mL). The organic phases were combined and dried with sodium sulfate before filtration. The solvent was removed from the filtrate leaving the acid sulfonamide. HMPSA and HDESA were further purified via short path distillation under vacuum. HFPSA and HFBSA were sublimed under vacuum or recrystallized from the vapor phase. Characterization data for exemplary acid sulfonamides of the present technology is provided below, including NMR spectroscopy and differential scanning calorimetry (DSC).

HMPSA (methoxypropyl trifluoromethylsulfonyl amide): After the extraction the HMPSA was further purified via vacuum distillation. The distillate was collected at 105° C. $H^1$ NMR (600 MHz, $CD_3CN$) δ 6.57 (s, 1H), 3.42 (t, J=5.9 Hz, 2H), 3.31 (t, J=6.8 Hz, 2H), 3.28 (s, 3H), 1.79 (p, J=6.4 Hz, 2H); $F^{19}$ NMR (564 MHz, $CD_3CN$) δ−78.7 (s); M.P.=−0.40° C. (calculated from D.S.C.)

HDESA (dimethoxyethyl trifluoromethylsulfonyl amide): After the extraction the HDESA was further purified via vacuum distillation. The distillate was collected at 120° C. $H^1$ NMR (600 MHz, $CD_3CN$) δ 6.67 (s, 1H), 4.41 (t, J=5.3 Hz, 1H), 3.37 (s, 6H), 3.29 (d, J=5.3 Hz, 2H); $F^{19}$ NMR (564 MHz, $CD_3CN$) δ−78.7 (s); M.P.=22.4° C. (calculated from D.S.C.)

HFPSA (pentafluoropropyl trifluoromethylsulfonyl amide): After the extraction the HFPSA was further purified via sublimation or vapor phase recrystallization. $H^1$ NMR (600 MHz, $CD_3CN$) δ 7.40 (s, 1H), 3.98 (t, J=14.8 Hz, 2H); $F^{19}$ NMR (564 MHz, $CD_3CN$) δ−78.7 (s), −84.7, −122.7; M.P.=47.5° C. (calculated from D.S.C.)

HFBSA (heptafluorobutyl trifluoromethylsulfonyl amide): After the extraction the HFBSA was further purified via sublimation or vapor phase recrystallization. $H^1$ NMR (600 MHz, $CD_3CN$) δ 7.42 (s, 1H), 4.02 (t, J=15.5 Hz, 2H); $F^{19}$NMR (564 MHz, $CD_3CN$) δ−78.6 (s), −81.6, −119.6, −128.0; M.P.=66.9° C. (calculated from D.S.C.)

Synthesis of Sulfonamide Salts The acid sulfonamide was converted to the lithium salt by reaction with a slight excess of LiH in acetonitrile. The reaction was performed under argon atmosphere and stirred for 12 hours. Because LiH is insoluble in acetonitrile, the excess was filtered off. After the solvent was removed, the salt was dried under vacuum at 90° C. overnight and stored in an argon filled glove box.

Synthesis of the sodium salt may be accomplished by sodium hydride or sodium carbonate via a similar procedure. Similarly, the K+, Rb+, and Cs+ salts may be accomplished from an acid sulfonamide via the appropriate alkali metal carbonate, as illustrated in the synthesis of KMPSA below in Scheme 1.

Scheme 1.

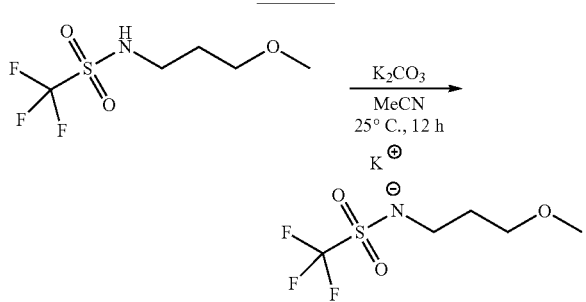

Specifically for KMPSA, the acid sulfonamide (HMPSA) was converted to the potassium salt by reaction with a 3-fold excess of $K_2CO_3$ in acetonitrile. The reaction was performed under argon atmosphere and stirred for 12 hours. Since K$_2$CO$_3$ is insoluble in acetonitrile, the excess was filtered off. After the solvent was removed, the salt was dried under vacuum at 90° C. overnight and stored in an argon filled glove box. KMPSA was originally reported in Lascaud, S.; Perrier, M.; Vallee, A.; Besner, S.; Prud, J.; Armand, M.; Vallke, A. "Phase Diagrams and Conductivity Behavior of Poly(Ethylene Oxide)-Molten Salt Rubbery Electrolytes" *Macromolecules* 1994, 27, 7469-7477, but only its application to polymer electrolytes was explored.

Ionic Conductivity Measurements A homemade conductivity cell was constructed with two polished stainless steel parallel plates (~0.3 cm$^2$) separated by ~0.2 cm in a Teflon cup. The entire cell was placed in a sealed vial to minimize electrolyte evaporation. To calibrate the cell constant, two conductivity standards (Sigma Aldrich) were used, 25 and 147 mhos/cm. The calibrated cell constant was calculated to be 0.706 cm'±0.008 cm$^{-1}$. 60 µL of electrolyte were placed in the cell and the entire cell was placed in an aluminum heating block set to 25° C.±0.1° C. The cell was held at 25° C. for 15 min prior to measurement. The electrochemical impedance spectrum was collected from 1 MHz to 0.5 Hz with an AC amplitude of 10 mV. The electrolyte resistance was taken as the impedance where the phase angle is as close to 0° C. as possible in order to minimize any contribution from capacitance or inductance. All conductivity measurements were performed in an argon filled glove box.

Cyclic Voltammetry Measurements The electrochemical stability window of each concentrated electrolyte was measured in a 3-electrode cell using cyclic voltammetry (CV). The working electrode was platinum metal with an area of 0.031 cm$^2$. The counter electrode was lithium metal. The reference electrode was a silver wire and the potential was calibrated in each electrolyte by measuring the Li$^+$/Li plating stripping potential. The scan rate for each CV measurement was 50 mV/s. The Al dissolution resistance was measured by cyclic voltammetry of a 2-electrode Li||Al CR2032 coin cell. The potential was swept from 2 V to 6.1 V for a total of 5 cycles. The cell consisted of Li foil and aluminum foil (1.77 cm$^2$) separated by a 25 µm trilayer celgard membrane (polypropylene-polyethylene-polypropylene).

Linear Sweep Voltammetry Measurements The electrochemical stability window of each concentrated electrolyte was measured in a 3-electrode cell using linear sweep voltammetry (LSV). The working electrode was platinum metal with an area of 0.031 cm$^2$. The counter electrode was potassium metal. The reference electrode was a silver wire and the potential was calibrated in each electrolyte by measuring the K$^+$/K plating stripping potential. The scan rate for each LSV measurement was 50 mV/s.

Potassium Oxygen Battery The full cell was assembled in the following manner: stainless steel base, K metal, glassy fiber separator (Whatman, GF/A), Celgard 2340 separator, glassy fiber separator (Whatman, GF/D), carbon paper (Avcarb P50), stainless steel current collector, and two stainless steel rings for a gas diffusion layer. The discharge and charge current was fixed at 67 µA/cm$^2$.

Results and Discussion

Figure 1A:
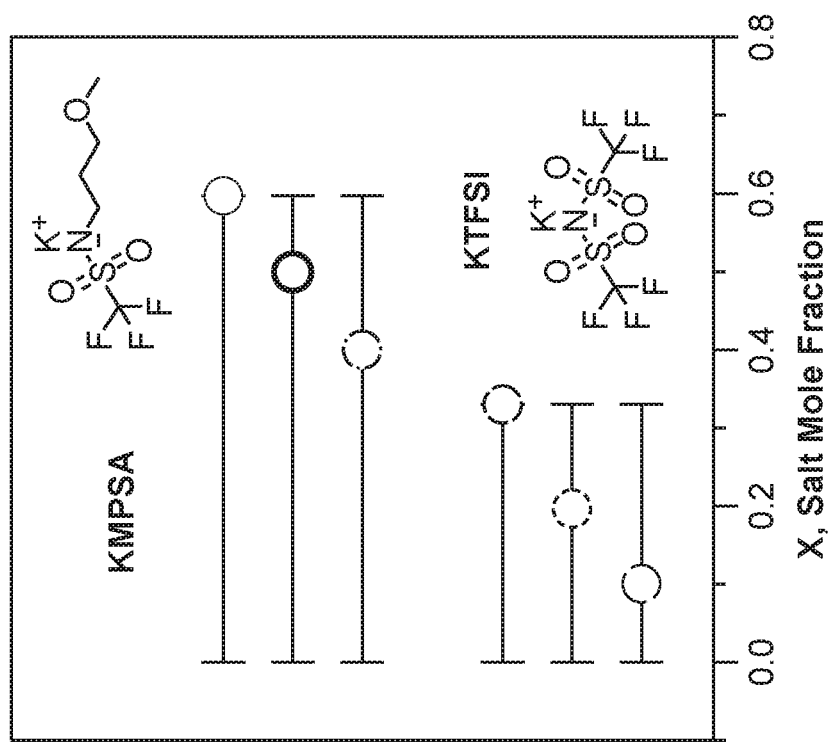

The stability and conductivity were investigated as a function of concentration (expressed in mol fraction XKMPSA), as typical concentrated electrolyte see benefits in stability at the cost of ionic conductivity.[12] For comparison, different concentrations of the symmetric sulfonamide salt, KTFSI, were also included in the electrochemical window characterization. The mol fraction of KTFSI can only reach ~0.34 X, whereas KMPSA can reach 0.6 X. To the best of the author's knowledge, this results in the highest reported solubility of any potassium salt in ether electrolyte. At high concentrations the positive electrochemical stability window for KMPSA electrolyte is increased when compared to that of KTFSI and is shown in FIGS. 1A-1B. This may be due to the lack of free DME solvent molecules (uncoordinated with potassium). This results in the properties being more similar to an ionic liquid or molten salt which are known for their large electrochemical windows.

Figure 2:
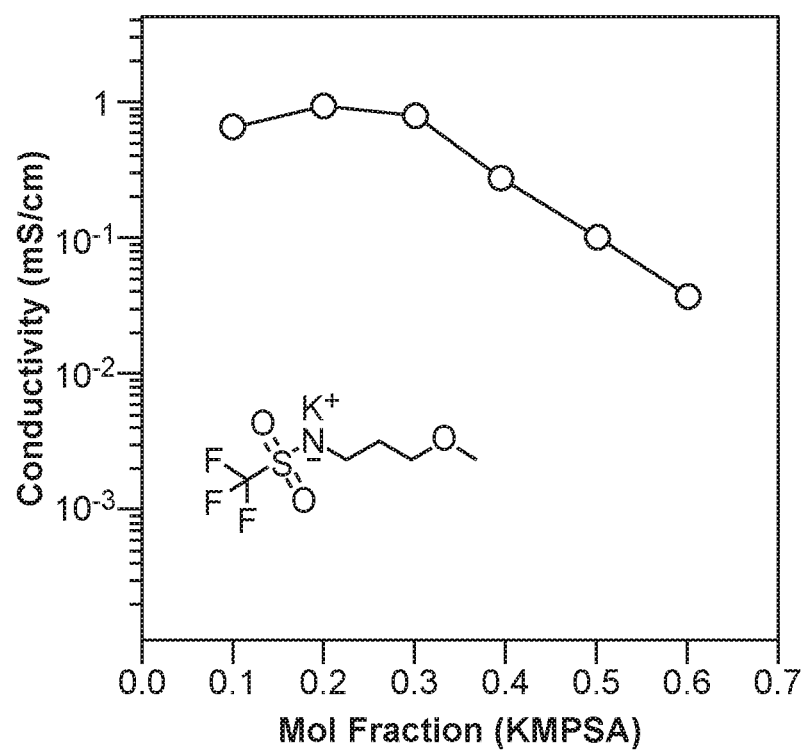
FIG. 2 illustrates the ionic conductivity of KMPSA in a DME electrolyte with increasing concentration, according to the working examples.

The benefit of high solubility translates to a higher conductivity than the molten salt while retaining a low vapor pressure and high electrochemical stability. As shown in FIG. 2 the ionic conductivity decreases with increasing concentration. The advantage in moving from molten salt to a salt-in-solvent is the increased ionic conductivity. For example, the ionic conductivity of 0.6×KMPSA/DME electrolyte (25° C., 0.037 mS/cm) is over an order of magnitude higher than the molten salt (45° C., 0.003 mS/cm).

Figure 3A:
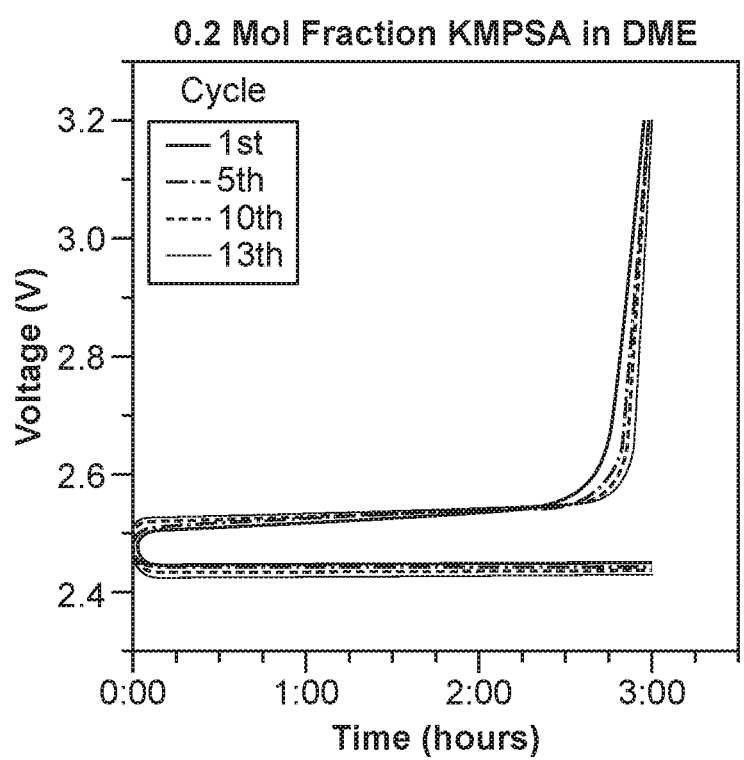
FIGS. 3A-3C provide discharge curves for several cycles for potassium-oxygen batteries with different concentrations of KMPSA.
Figure 3B:
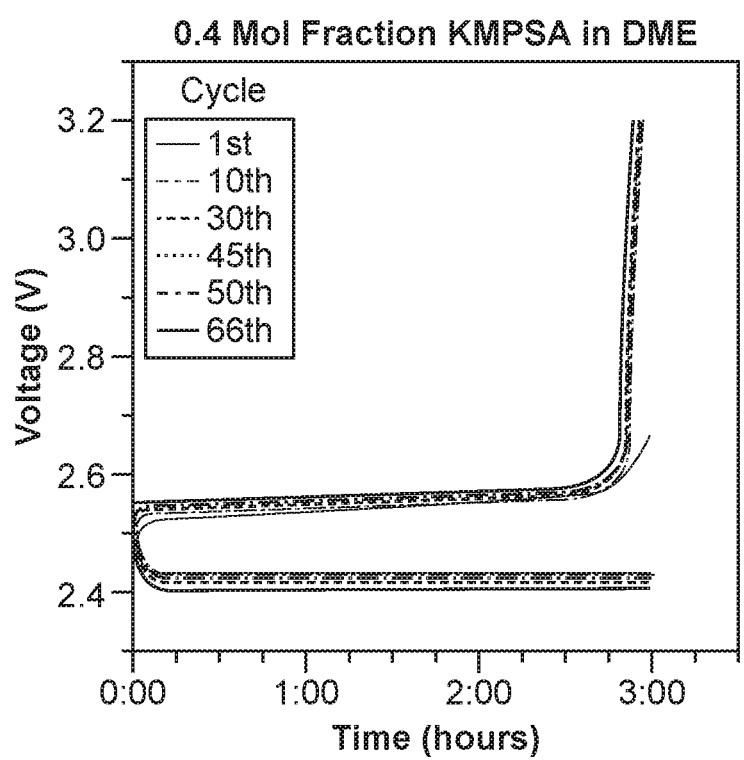
Figure 3C:
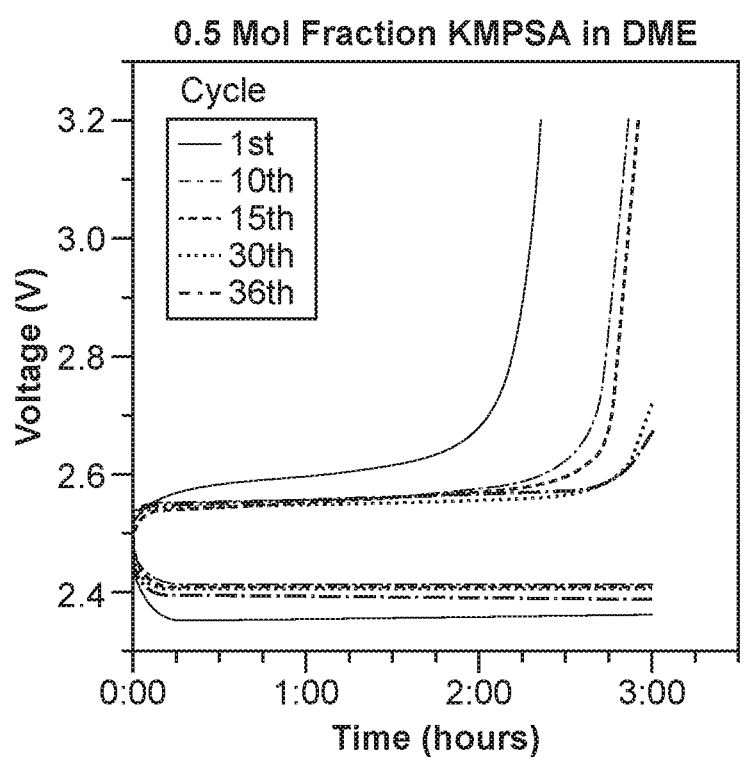

In light of the high solubility of and excellent electrochemical stability, the KMPSA/DME electrolyte was explored for use in a potassium-oxygen battery. A typical potassium-oxygen battery with KPF$_6$ electrolyte can demonstrate about 10 cycles without the presence of any K$^+$-Nafion membrane to limit the oxygen crossover. With the membrane, the cycle life can be increased to about 50 cycles.[11,18] In the case of a KMPSA/DME electrolyte, no K$^+$-Nafion membrane was used in order to fully probe the ability of the concentrated electrolyte to stabilize the metal electrode, decrease oxygen crossover and increase cycle life. The KMPSA/DME electrolyte was studied at different concentrations of 0.2 X, 0.4× and 0.5× mole factions with respect to the salt. The resulting discharge curves for several cycles are shown in FIGS. 3A-3C. The lowest mol fraction, 0.2× electrolyte fails within ~10 cycles, which is in line with other reports without using the K$^+$-Nafion membrane.[13] As the salt concentration is increased to 0.4× and 0.5× the cycle life increases significantly. When using the 0.4× KMPSA/DME electrolytes, the potassium-oxygen battery can cycle for over 60 cycles without the use of any K$^+$-Nafion membrane. Currently, this cycle life is one of highest reported, of any potassium-oxygen battery, with or without the use of a K$^+$-Nafion membrane.[16] Another interesting note is the low overpotential even in the case of the highest concentration, 0.5×KMPSA DME electrolytes. The 0.5×KMPSA electrolyte has one of the lowest ionic conductivities of ~0.1 mS/cm$^2$ and thus expected to have a larger overpotential in the potassium-oxygen battery. However, when compared to a previous study with 1 M KTFSI the overpotential in KMPSA based electrolyte is lower.[13] This is despite the fact that the ionic conductivity of the KMPSA/DME is expected to be one order of magnitude lower (based on reported values for LiTFSI).

Thus, a highly soluble potassium salt was synthesized by a general method, which can be used for generating a wide variety of asymmetric sulfonamide salts. The KMPSA salt exhibited formation of a solvent-in-salt electrolyte with DME. This allowed the electrolyte to access the concentration regime between that of typical concentrated electrolytes and molten salt. Additionally, this allowed for the electrolyte to have a higher ionic conductivity than the molten KMPSA salt, while retaining some of the beneficial properties associated with molten salt electrolytes such as low vapor pressure and large electrochemical windows. The KMPSA/SME electrolyte was also evaluated in a potassium-oxygen battery where it was found to increase cycle life and promote formation of a more conductive and/or thinner SEI than that of 1 M KTFSI.

Figure 4:
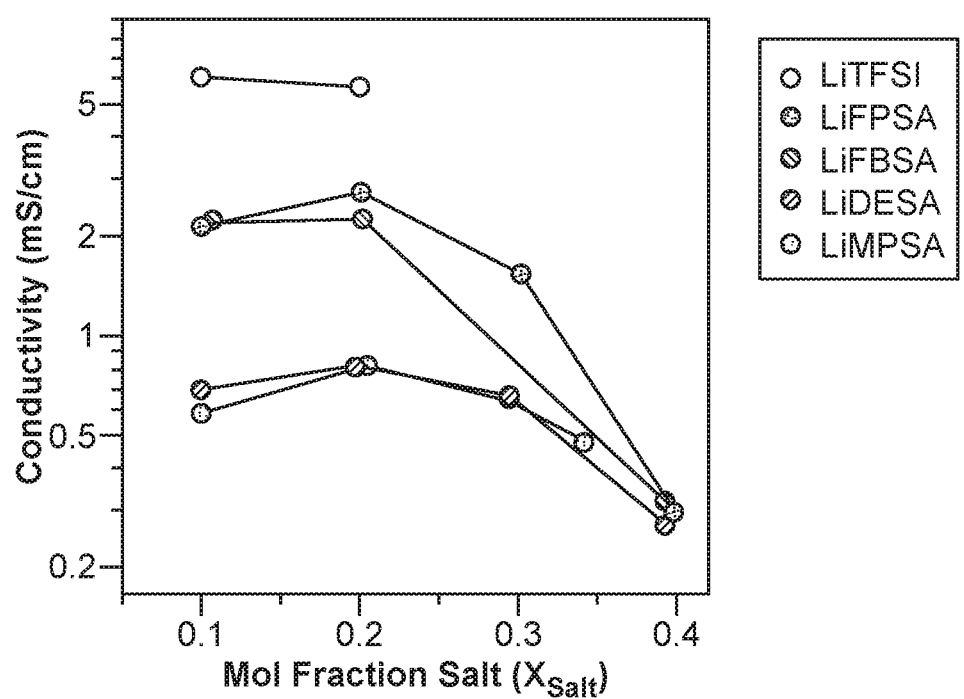
FIG. 4 provides the ionic conductivity of sulfonamide salts plotted as a function mole fraction in diglyme, according to the working examples.

In order to probe structure-property relationships among sulfonamide salts, the ionic conductivity was investigated in diglyme solvent and compared with that of LiTFSI. Ethers such as diglyme have strong Lewis basicity, high chemical stability and can dissolve lithium salts via Li+ cation coordination by the lone pair on the oxygen atom.[105] However, the solubility of LiTFSI is relativity low and cannot access the concentrated electrolyte regime. This is in stark contrast to all of the sulfonamide salts investigated here. The solubility of the salts increase in the order LiTFSI<LiMPSA<LiFBSA≈LiFPSA≈LiDESA. To the best of the inventors' knowledge, in ether solvent, these sulfonamide salts have the highest solubility among any lithium salt (0.4× salt, molar ratio diglyme: Salt 1:1.5). The ionic conductivity of these electrolytes were investigated as a function of concentration (FIG. 4). The sulfonamide based electrolytes span a much larger concentration range of up to 0.4 mol fraction, where LiTFSI can only be increased up to 0.2 mol fraction. In general, higher concentration electrolytes are accompanied with lower ionic conductivities.[103] When compared with reported ionic conductivities of concentrated LiTFSI in carbonate electrolytes, the ionic conductivity of all the sulfonamide electrolytes are slightly improved (i.e. >0.5 mS/cm$^2$ at 0.33 mol fraction).[106] The salts with fluorinated side chains, like LiFPSA and LiFBSA have a higher ionic conductivity than those with an incorporated ether group. This could be due to reduced viscosity of the electrolytes with fluorinated derivatives as well as the ability of the ether oxygen within LiMPSA and LiDESA to coordinate the lithium cation even at low concentrations in a similar fashion to that of diglyme solvent. Interestingly, no matter the functionality of the sulfonamide salt, the trend in ionic conductivity is very similar. At a concentration of 0.4 mol fraction, all the electrolytes seem to converge to a similar value.

Figure 5:
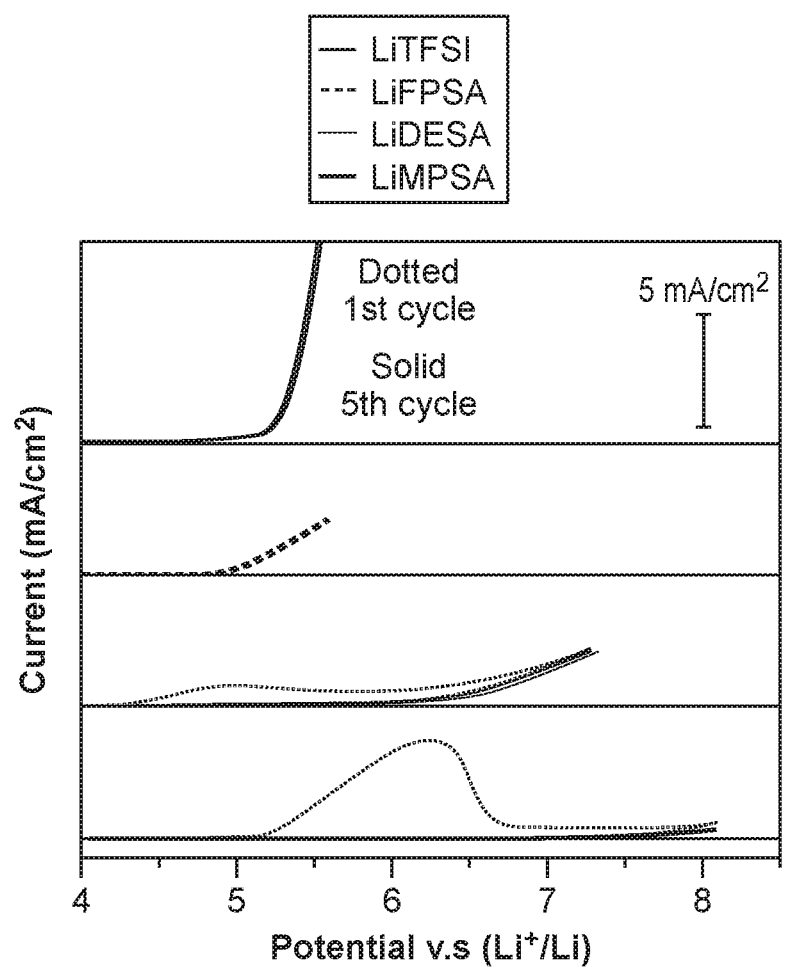
FIG. 5 provides the oxidative stability window of different electrolytes in diglyme, according to the working examples: 0.20 mol fraction ("x") LiTFSA, 0.40×LiFPSA, 0.40×LiDESA, 0.33×LiMPSA at a scan rate of 50 mV/s, with a Pt working electrode.

Since it has been reported that increasing the salt concentration also improves the electrochemical window,[103,107] the stability window of each electrolyte at its highest concentration was examined. In a 3-electrode cell using a platinum working electrode, Li metal counter and a silver wire reference to avoid electrolyte contamination, cyclic voltammetry was used to examine the oxidative window. Multiple scans were collected to see if there was any change with repeat cycling to highly positive voltages (FIG. 5). As a comparison, the most concentrated possible LiTFSI solution (0.2 mol fraction) was also tested. The LiTFSI electrolyte showed one of the lowest stabilities with rapid decomposition occurring above 5 V. The LiFPSA 0.4 mol fraction electrolyte showed the smallest stability window despite being more fluorinated and more concentrated. One of the most interesting results is the LiMPSA electrolyte. It has a lower concentration of 0.33 mol fraction, yet it appears to have one of the highest stabilities. The first scan of LiTFSI and LiFPSA electrolytes overlap with the next 4 scans. However, LiMPSA and LiDESA have an oxidative current on the first cycle and all subsequent cycles show high stability even out to very positive potentials (i.e., 6-7 V).

In the case of LiTFSI and LiFPSA decomposition occurs continuously. However, in LiMPSA and LiDESA electrolytes, a surface passivation layer could be formed which is then stable in subsequent scans. The current onset for LiMPSA occurs near the oxidative decomposition voltage of the LiTFSI and LiFPSA electrolytes. LiMPSA and LiDESA showed similar behavior on the first scan whereas LiFPSA did not, which suggests it may be influenced by the similarity in functional groups between the salt and solvent. Oxidative current on the 1st scan could be due to solvent decomposition or salt decomposition. In solvent decomposition, the favorable passivation may stem from interaction between the salt ether group and the ether solvent. In both cases, we believe that passivation is aided by the asymmetric structure and surfactant like nature of LiMPSA/LiDESA which result in preferential orientation at the electrode surface.

Aluminium dissolution is heavily dependent on the anion. For example, several commercial salts such as lithium trifluoromethanesulfonate (LiOTf), LiTFSI and lithium hexafluorophosphate (LiPF$_6$) exhibit wide variation in their ability to resist Al anodic dissolution. In LiOTf based electrolytes with carbonate solvent, aluminum undergoes anodic dissolution above 2.7 V (vs. Li+/Li) and develops significant pitting above 3.0 V (vs. Li+/Li).[108] LiTFSI based electrolytes have slightly higher resistance, with anodic dissolution occurring above 3.5 V (vs. Li+/Li).[106,108,109] One proposed mechanism for this dissolution is formation of Al(TFSI)$_3$ species at the surface followed by solvation.[109,110] Higher resistance to Al dissolution can currently be achieved with LiPF$_6$ electrolyte. Its thermal decomposition and/or hydrolysis products are believed to facilitate formation of AlF or AlOF species which are insoluble in the electrolyte.[108,109] Therefore a passivation layer is formed rather than dissolving as is the case with LiTFSI electrolytes.[111] Despite this positive effect, the decomposition and hydrolysis products can have deleterious effects on the performance of the battery. The instability of PF$_6$-in water can lead to HF formation and promote unwanted side reactions.[112,113] Therefore, if Al dissolution can be suppressed in sulfonimide based electrolytes, they become attractive alternatives to LiPF$_6$ due to their increased thermal stability and resistance to hydrolysis.[108]

One strategy for increasing the resistance of sulfonamide based electrolytes to aluminum dissolution has been small synthetic modifications. Krause et. al. showed that lengthening the perfluoro alkyl chains results in slightly enhanced dissolution resistance for salts with larger molecular weights.[114] Additionally, highly concentrated electrolytes can also be a strategy for improved aluminum dissolution resistance. Both Matsumoto et. al. and Wang et. al. have shown that high concentrations of LiTFSI or LiFSI, respectively, can result in significant suppression of aluminum dissolution.[107,113]

Figure 6:
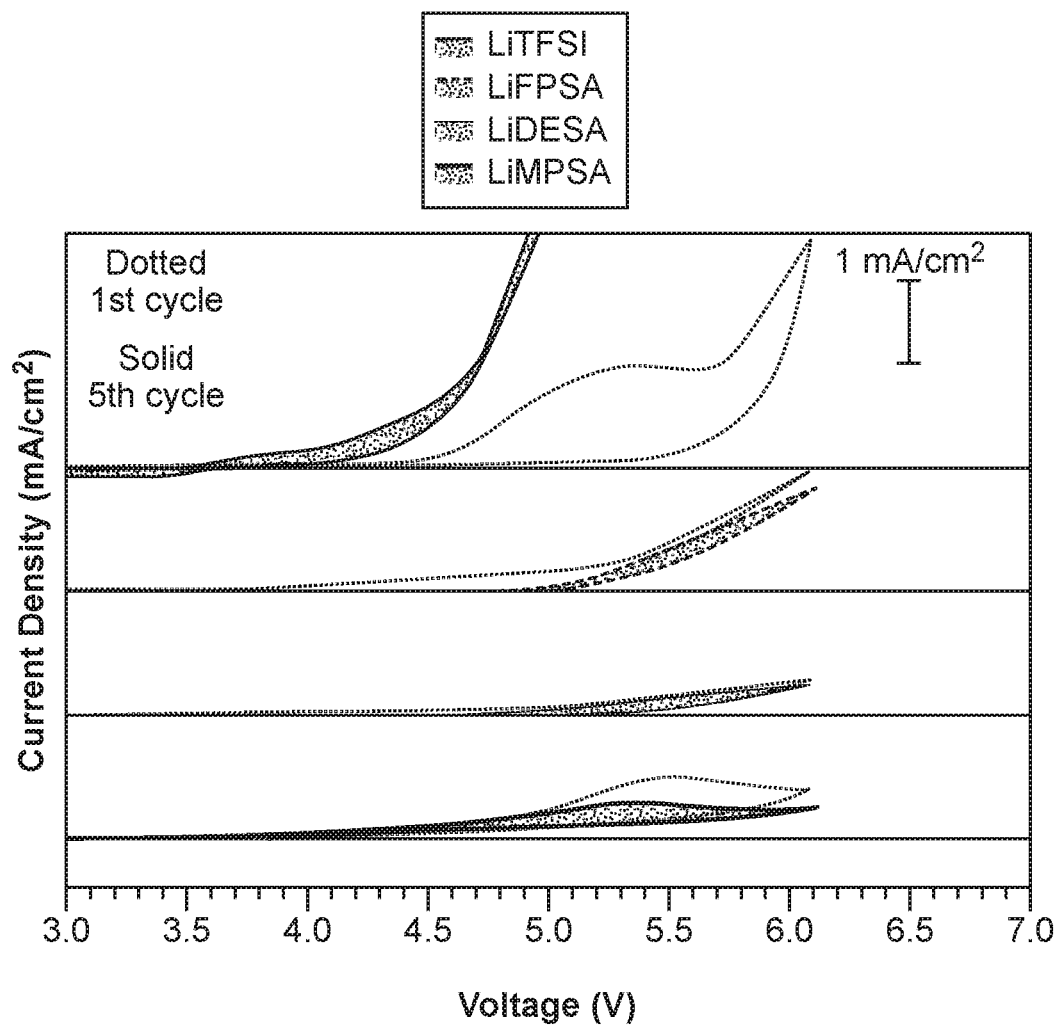
FIG. 6 provides the results of cyclic voltammetry of Li∥Al anodic dissolution cells swept from 2-6.1 V at 50 my/s, according to the working examples. 1st cycle is shown as a dotted line and 5th cycle as a solid line.

The high solubility and enhanced electrochemical windows indicate the sulfonamide electrolytes have potential in suppression of anodic Al dissolution. In order to test this hypothesis, Li||Al coin cells were assembled and the voltage of the cell swept from 2 V-6.1 V for 5 cycles. For comparison, the results of the 1st and 5th cycle were overlapped (FIG. 6). From this result, LiTFSI shows the highest dissolution rates of any electrolyte tested in this study. In contrast, all of the sulfonamide electrolytes show a significant improvement. After the first cycle, both LiFPSA and LiDESA require over 5 V in order for dissolution to occur, and more importantly, the oxidative current decreases with cycle number. In spite of LiFPSA having a lower stability window, this salt still shows a significant improvement in its ability to resist Al dissolution. More importantly, LiFPSA and LiDESA both show similar oxidative current to LiPF$_6$ (1M in EC/DMC) electrolyte at 5 volts.

Figure 7:
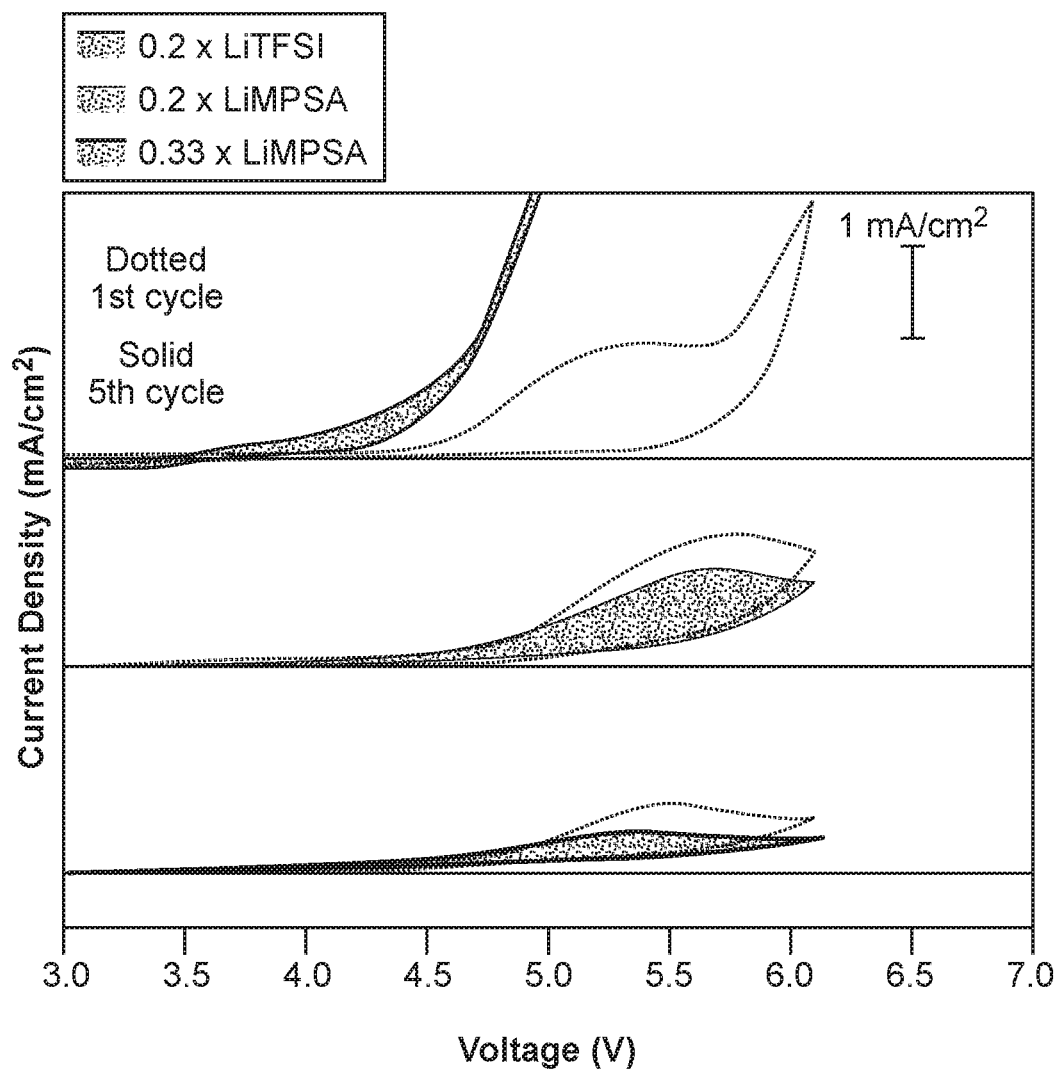
FIG. 7 provides the results of cyclic voltammetry of Li∥Al Anodic dissolution cells with different concentrations of LiMPSA.

Additionally, the LiMPSA electrolyte was evaluated at lower concentrations in order to probe the relative importance of anion structure and concentration. In FIG. 7 the oxidative current is lowered with increased concentration but the overall profile compared to LiTFSI is still improved despite the similar concentration. Therefore, the Al dissolution resistance should be dependent on both anion structure, as well as concentration.

After testing on the Li∥Al coin cells was complete, the cell was disassembled and the Al electrode was examined using an optical microscope. Examination of the surface revealed a significant amount of aluminum pits on the electrode for the cell with LiTFSI. Some pits were observed for the LiFPSA electrolyte, however they are much smaller and more dispersed on the aluminium electrode. LiMPSA and LiDESA both show a very uniform Al surface with negligible pitting. One possibility is the oxidation current for these salts stem from formation of a passivation layer as previously discussed in regard to FIG. 5.

Structure tuning of the salt anion has also been reported by Huang et. al, where fluorinated aryl sulfonamide tagged (FAST) salts were reported as a synthetically tunable platform that can allow investigations into many structure-property relationships.[115] However, the FAST salts typically suffer from low solubility. Similarly, solvents were also developed using a similar method by Shyamsunder et. al where a secondary amine and triflic anhydride were used to yield highly stable triflamide solvents.[116] These methods together with that presented here provide a platform for designer electrolytes in which the salt and solvent can be tailor made for the desired application.

In conclusion, these examples evidence the significant advantages of the electrolyte salts of the present technology as well as non-aqueous electrolytes and batteries incorporating such salts.

While certain embodiments have been illustrated and described, a person with ordinary skill in the art, after reading the foregoing specification, can effect changes, substitutions of equivalents and other types of alterations to the batteries and compounds of the present technology as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. An electrolyte salt according to Formula I

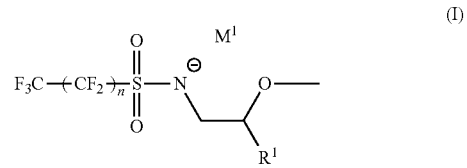

wherein
R¹ is H or OCH₃;
M¹ is Li⁺, Na⁺, K⁺, Rb⁺, or Cs⁺; and
n is 0, 1, or 2;
provided that when R¹ is OCH₃ and n is 0, M¹ is not Lit B. An electrolyte salt according to Formula II

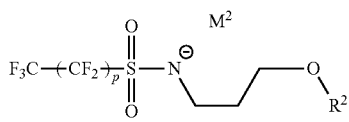
(II)

wherein
R² is CH₃ or CH(CH₃)₂;
M² is Li⁺, Na⁺, K⁺, Rb⁺, or Cs⁺; and
p is 0, 1, or 2;
provided that when R² is CH₃, p is not 0.

C. An electrolyte salt according to Formula III

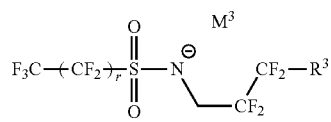
(III)

wherein
R³ is F, CF₃, or CF₂CF₃;
M³ is Li⁺, Na⁺, K⁺, Rb⁺, or Cs⁺; and
r is 0, 1, or 2.

D. A battery comprising a cathode; an anode; and a non-aqueous electrolyte, wherein the non-aqueous electrolyte comprises a solvent and at least one electrolyte salt according to Formula III, Formula IV, or Formula V

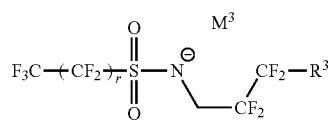
(III)

wherein in Formula III
R³ is F, CF₃, or CF₂CF₃;
M³ is Li⁺, Na⁺, K⁺, Rb⁺, or Cs⁺; and
r is 0, 1, or 2;

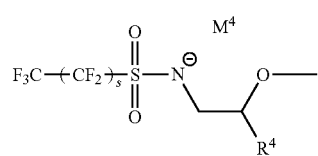
(IV)

wherein in Formula IV
R⁴ is H or OCH₃;
M⁴ is Li⁺, Na⁺, K⁺, Rb⁺, or Cs⁺; and
s is 0, 1, or 2;

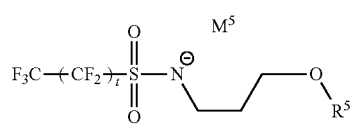
(V)

wherein in Formula V
R⁵ is CH₃ or CH(CH₃)₂;
M⁵ is Li⁺, Na⁺, K⁺, Rb⁺, or Cs⁺; and
t is 0, 1, or 2.

E. The battery of Paragraph D, wherein when R⁴ is OCH₃ and s is 0, M⁴ is not Lit F. The battery of Paragraph D or Paragraph E, wherein when R⁵ is CH₃, t is not 0.

G. The battery of any one of Paragraphs D-F, wherein the solvent comprises dimethoxyethane, digylme, triglyme, tetraglyme, dimethylsulfoxide (DMSO), or a mixture of any two or more thereof.

H. The battery of any one of Paragraphs D-G, wherein the battery is a secondary battery.

I. The battery of any one of Paragraphs D-H, wherein the cathode comprises a positive electroactive material.

J. The battery of any one of Paragraphs D-I, wherein the cathode comprises an olivine-based material, a fluorinated olivine-based material, an iron-cyano complex, a transition metal oxide, a transition metal sulfide, a transition metal halide, or a combination of any two or more thereof.

K. The battery of any one of Paragraphs D-H, wherein the cathode is an air cathode.

L. The battery of Paragraph K, wherein the air cathode comprises a porous carbon material.

M. The battery of Paragraph K or Paragraph L, wherein the air cathode further comprises a metal oxide.

N. The battery of any one of Paragraphs K-M, wherein the cathode further comprises a binder.

O. The battery of any one of Paragraphs D-N, wherein the at least one electrolyte salt is at a concentration in the solvent of about 0.05 M to about 1.0 M.

Other embodiments are set forth in the following claims, along with the full scope of equivalents to which such claims are entitled.

REFERENCES (1) Dunn, B.; Kamath, H.; Tarascon, J.-M. Electrical Energy Storage for the Grid: A Battery of Choices. *Science,* 2011, 334 (6058), 928-935.

(2) Goodenough, J. B.; Park, K. S. The Li-Ion Rechargeable Battery: A Perspective. *J. Am. Chem. Soc.* 2013, 1167-1176.

(3) Peled, E.; Golodnitsky, D.; Hadar, R.; Mazor, H.; Goor, M.; Burstein, L. Challenges and Obstacles in the Development of Sodium-Air Batteries. *J. Power Sources* 2013, 244, 771-776.

(4) Yadegari, H.; Sun, Q.; Sun, X. Sodium-Oxygen Batteries: A Comparative Review from Chemical and Electrochemical Fundamentals to Future Perspective. *Adv. Mater.* 2016, 7065-7093.

(5) Landa-Medrano, I.; Li, C.; Ortiz-Vitoriano, N.; Ruiz De Larramendi, I.; Carrasco, J.; Rojo, T. Sodium-Oxygen Battery: Steps Toward Reality. *J. Phys. Chem. Lett.* 2016, 7, 1161-1166.

(6) Li, L.; Chang, Z.; Zhang, X.-B. Recent Progress on the Development of Metal-Air Batteries. *Adv. Sustain. Syst.* 2017, 1, 1700036.

(7) Ren, X.; Wu, Y. A Low-Overpotential Potassium-Oxygen Battery Based on Potassium Superoxide. *J. Am. Chem. Soc.* 2013, 135 (8), 2923-2926.

(8) Abraham, K. M. Electrolyte-Directed Reactions of the Oxygen Electrode in Lithium-Air Batteries. *J. Electrochem. Soc.* 2014, 162, A3021-A3031.

(9) Merz, P.; Schmidt, M.; Felser, C.; Jansen, M. Thermo-Analytical Investigations on the Superoxides A O 2 (A=K, Rb, Cs), Revealing Facile Access to Sesquioxides A 4 O 6. *Zeitschrift für Anorg. and Allg. Chemie* 2017, 643, 544-547.

(10) Vol'nov, I. I. *Peroxides, Superoxides, and Ozonides of Alkali and Alkaline Earth Metals*; Petrocelli, A. W., Ed.; Springer US: Boston, MA, 1966.

(11) Ren, X.; Lau, K. C.; Yu, M.; Bi, X.; Kreidler, E.; Curtiss, L. A.; Wu, Y. Understanding Side Reactions in K—O2 Batteries for Improved Cycle Life. *ACS Appl. Mater. Interfaces* 2014, 6 (21), 19299-19307.

(12) Yamada, Y.; Yamada, A. Review—Superconcentrated Electrolytes for Lithium Batteries. *J. Electrochem. Soc.* 2015, 162 (14), A2406-A2423.

(13) Ren, X.; He, M.; Xiao, N.; Mcculloch, W. D.; Wu, Y. Greatly Enhanced Anode Stability in K-Oxygen Batteries with an In Situ Formed Solvent- and Oxygen-Impermeable Protection Layer. *Adv. Energy Mater.* 2017, 7,1601080

(14) He, M.; Lau, K. C.; Ren, X.; Xiao, N.; McCulloch, W. D.; Curtiss, L. A.; Wu, Y. Concentrated Electrolyte for the Sodium-Oxygen Battery: Solvation Structure and Improved Cycle Life. *Angew. Chemie—Int. Ed.* 2016, 55, 15310-15314.

(15) Xiao, N.; McCulloch, W. D.; Wu, Y. Reversible Dendrite-Free Potassium Plating and Stripping Electrochemistry for Potassium Secondary Batteries. *J. Am. Chem. Soc.* 2017, 139, 9475-9478.

(16) Xiao, N.; Gourdin, G.; Wu, Y. Electrolyte Chemistry for Simultaneous Stabilization of Potassium Metal and Superoxide in K—$O_2$ Batteries. *Angew. Chemie* 2018, DOI: 10.1002/ange.201804115

(17) Lascaud, S.; Perrier, M.; Vallee, A.; Besner, S.; Prud, J.; Armand, M.; Vallke, A. Phase Diagrams and Conductivity Behavior of Poly(Ethylene Oxide)-Molten Salt Rubbery Electrolytes. *Macromolecules* 1994, 27, 7469-7477.

(18) Yu, W.; Lau, K. C.; Lei, Y.; Liu, R.; Qin, L.; Yang, W.; Li, B.; Curtiss, L. A.; Zhai, D.; Kang, F. Dendrite-Free Potassium-Oxygen Battery Based on a Liquid Alloy Anode. *ACS Appl. Mater. Interfaces* 2017, 9, 31871-31878.

(101) Deng, D. Li-Ion Batteries: Basics, Progress, and Challenges. *Energy Sci. Eng.* 2015, 3 (5), 385-418.

(102) Kraytsberg, A.; Ein-Eli, Y.; Kraytsberg, A.; Ein-Eli, Y. Higher, Stronger, Better . . . A Review of 5 Volt Cathode Materials for Advanced Lithium-Ion Batteries. *Adv. Energy Mater.* 2012, 2 (8), 922-939.

(103) Yamada, Y.; Yamada, A. Review—Superconcentrated Electrolytes for Lithium Batteries. *J. Electrochem. Soc.* 2015, 162 (14), A2406-A2423.

(104) Lascaud, S.; Perrier, M.; Vallee, A.; Besner, S.; Prud, J.; Armand, M.; Vallke, A. Phase Diagrams and Conductivity Behavior of Poly(Ethylene Oxide)-Molten Salt Rubbery Electrolytes. *Macromolecules* 1994, 27 (25), 7469-7477.

(105) Yamada, Y.; Yaegashi, M.; Abe, T.; Yamada, A. A Superconcentrated Ether Electrolyte for Fast-Charging Li-Ion Batteries. *Chem. Commun.* 2013, 49 (95), 11194.

(106) McOwen, D. W.; Seo, D. M.; Borodin, 0.; Vatamanu, J.; Boyle, P. D.; Henderson, W. A. Concentrated Electrolytes: Decrypting Electrolyte Properties and Reassessing Al Corrosion Mechanisms. *Energy Environ. Sci.* 2014, 7 (1), 416-426.

(107) Wang, J.; Yamada, Y.; Sodeyama, K.; Chiang, C. H.; Tateyama, Y.; Yamada, A. Superconcentrated Electrolytes for a High-Voltage Lithium-Ion Battery. *Nat. Commun.* 2016, 7 (May), 12032.

(108) Xu, K. Nonaqueous Liquid Electrolytes for Lithium-Based Rechargeable Batteries. *Chem. Rev.* 2004, 104 (10), 4303-4417.

(109) Yang, H.; Kwon, K.; Devine, T. M.; Evans, J. W. Aluminum Corrosion in Lithium Batteries An Investigation Using the Electrochemical Quartz Crystal Microbalance Aluminum Corrosion in Lithium Batteries. *J. Electrochem. Soc.* 2000, 147 (12), 4399-4407.

(110) Kramer, E.; Schedlbauer, T.; Hoffmann, B.; Terborg, L.; Nowak, S.; Gores, H. J.; Passerini, S.; Winter, M. Mechanism of Anodic Dissolution of the Aluminum Current Collector in 1 M LiTFSI EC:DEC 3:7 in Rechargeable Lithium Batteries. *J. Electrochem. Soc.* 2012, 160 (2), A356-A360.

(111) Kanamura, K.; Umegaki, T.; Shiraishi, S.; Ohashi, M.; Takehara, Z. Electrochemical Behavior of Al Current Collector of Rechargeable Lithium Batteries in Propylene Carbonate with LiCF3 SO3, Li(CF3SO2])2]N, or Li(C4F 9SO 2)(CF 35O2)N. *J. Electrochem. Soc.* 2002, 149 (2), A185.

(112) Shieh, D. T.; Hsieh, P. H.; Yang, M. H. Effect of Mixed LiBOB and $LiPF_6$ salts on Electrochemical and Thermal Properties in LiMn2O4 batteries. *J. Power Sources* 2007, 174 (2), 663-667.

(113) Matsumoto, K.; Inoue, K.; Nakahara, K.; Yuge, R.; Noguchi, T.; Utsugi, K. Suppression of Aluminum Corrosion by Using High Concentration LiTFSI Electrolyte. *J. Power Sources* 2013, 231, 234-238.

(114) Krause, L. J.; Lamanna, W.; Summerfield, J.; Engle, M.; Korba, G.; Loch, R.; Atanasoski, R. Corrosion of Aluminum at High Voltages in Non-Aqueous Electrolytes Containing Perfluoroalkylsulfonyl Imides; New Lithium Salts for Lithium-Ion Cells. *J. Power Sources* 1997, 68 (2), 320-325.

(115) Huang, M.; Feng, S.; Zhang, W.; Giordano, L.; Chen, M.; Amanchukwu, C. V.; Anandakathir, R.; Shao-Horn, Y.; Johnson, J. A. Fluorinated Aryl Sulfonimide Tagged (FAST) Salts: Modular Synthesis and Structure—property Relationships for Battery Application. *Energy Environ. Sci.* 2018.

(116) Shyamsunder, A.; Beichel, W.; Klose, P.; Pang, Q.; Scherer, H.; Hoffmann, A.; Murphy, G. K.; Krossing, I.; Nazar, L. F. Inhibiting Polysulfide Shuttle in Lithium—Sulfur Batteries through Low-Ion-Pairing Salts and a Triflamide Solvent. *Angew. Chemie—Int. Ed.* 2017, 56 (22), 6192-6197.

What is claimed is:

1. An electrolyte salt according to Formula I

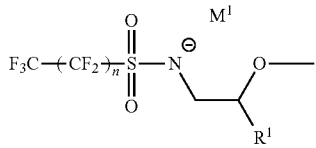  (I)

wherein
R$^1$ is OCH$_3$;
M$^1$ is Li$^+$, Na$^+$, K$^+$, Rb$^+$, or Cs$^+$; and
n is 0, 1, or 2;
provided that when n is 0, M$^1$ is not Li$^+$.

2. An electrolyte salt according to Formula II

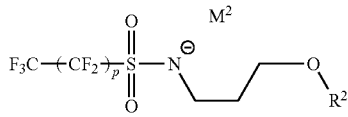  (II)

wherein
R$^2$ is CH$_3$ or CH(CH$_3$)$_2$;
M$^2$ is Li$^+$, Na$^+$, K$^+$, Rb$^+$, or Cs$^r$; and
p is 0, 1, or 2;
provided that when R$^2$ is CH$_3$, p is not 0.

3. An electrolyte salt according to Formula III

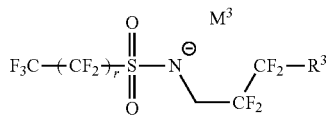  (III)

wherein
R$^3$ is F, CF$_3$, or CF$_2$CF$_3$;
M$^3$ is Li$^+$, Na$^+$, K$^+$, Rb$^+$, or Cs$^+$; and
r is 0, 1, or 2.

4. A battery comprising a cathode; an anode; and a non-aqueous electrolyte, wherein the non-aqueous electrolyte comprises a solvent and at least one electrolyte salt according to Formula III, Formula IV, or Formula V

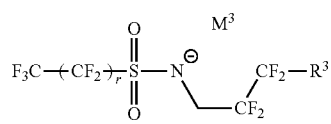  (III)

wherein in Formula III
R$^3$ is F, CF$_3$, or CF$_2$CF$_3$;
M$^3$ is Li$^+$, Na$^+$, K$^+$, Rb$^+$, or Cs$^+$; and
r is 0, 1, or 2;

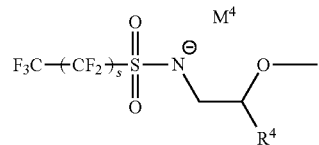  (IV)

wherein in Formula IV
R$^4$ is OCH$_3$;
M$^4$ is Li$^+$, Na$^+$, K$^+$, Rb$^+$, or Cs$^+$; and
s is 0, 1, or 2;

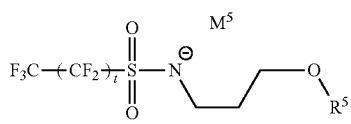  (V)

wherein in Formula V
R$^5$ is CH$_3$ or CH(CH$_3$)$_2$;
M$^5$ is Li$^+$, Na$^+$, K$^+$, Rb$^+$, or Cs$^+$; and
t is 0, 1, or 2.

5. The battery of claim 4, wherein when s is 0, M$^4$ is not Li$^+$.

6. The battery of claim 4, wherein when R$^5$ is CH$_3$, t is not 0.

7. The battery of claim 4, wherein the solvent comprises dimethoxyethane, digylme, triglyme, tetraglyme, dimethylsulfoxide (DMSO), or a mixture of any two or more thereof.

8. The battery of claim 4, wherein the battery is a secondary battery.

9. The battery of claim 4, wherein the cathode comprises a positive electroactive material.

10. The battery of claim 4, wherein the cathode comprises an olivine-based material, a fluorinated olivine-based material, an iron-cyano complex, a transition metal oxide, a transition metal sulfide, a transition metal halide, or a combination of any two or more thereof.

11. The battery of claim 4, wherein the cathode is an air cathode.

12. The battery of claim 11, wherein the air cathode comprises a porous carbon material.

13. The battery of claim 11, wherein the air cathode further comprises a metal oxide.

14. The battery of claim 11, wherein the cathode further comprises a binder.

15. The battery of claim 4, wherein the at least one electrolyte salt is at a concentration in the solvent of about 0.05 M to about 1.0 M.

16. An electrolyte salt according to Formula I

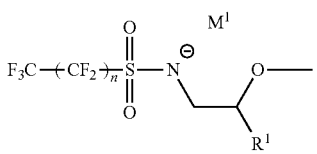  (I)

wherein
R$^1$ is H;
M$^1$ is Li$^+$, Na$^+$, K$^+$, Rb$^+$, or Cs$^+$; and
n is 1 or 2.

17. A battery comprising a cathode; an anode; and a non-aqueous electrolyte, wherein the non-aqueous electrolyte comprises a solvent and an electrolyte salt of claim 16.

18. The battery of claim 17, wherein the solvent comprises dimethoxyethane, digylme, triglyme, tetraglyme, dimethylsulfoxide (DMSO), or a mixture of any two or more thereof.

19. The battery of claim 17, wherein the cathode is an air cathode.

20. The battery of claim 17, wherein the at least one electrolyte salt is at a concentration in the solvent of about 0.05 M to about 1.0 M.

* * * * *